(12) United States Patent
Kiev et al.

(10) Patent No.: US 11,963,692 B2
(45) Date of Patent: Apr. 23, 2024

(54) BODY CAVITY ACCESS DEVICE

(71) Applicant: AOK Innovations, LLC, Lexington, KY (US)

(72) Inventors: Jon Kiev, Lexington, KY (US); Mindy Phung, Jamaica Plain, MA (US); Christopher Strahm, Deforest, WI (US)

(73) Assignee: AOK Innovations, LLC, Lexington, KY (US)

( * ) Notice: Subject to any disclaimer, the term of this patent is extended or adjusted under 35 U.S.C. 154(b) by 196 days.

(21) Appl. No.: 17/302,389

(22) Filed: Apr. 30, 2021

(65) Prior Publication Data

US 2022/0346821 A1 Nov. 3, 2022

(51) Int. Cl.
*A61B 17/32* (2006.01)
*A61B 17/34* (2006.01)
*A61B 17/00* (2006.01)

(52) U.S. Cl.
CPC .. *A61B 17/320016* (2013.01); *A61B 17/3423* (2013.01); *A61B 17/3496* (2013.01); *A61B 2017/0042* (2013.01)

(58) Field of Classification Search
CPC ........... A61B 17/3415; A61B 17/34; A61B 17/320016; A61B 17/3496; A61B 17/3423; A61B 2017/0042; A61B 17/3417
See application file for complete search history.

(56) References Cited

U.S. PATENT DOCUMENTS

| | | | |
|---|---|---|---|
| 4,535,773 | A | 8/1985 | Yoon et al. |
| 4,772,266 | A | 9/1988 | Groshong |
| 5,066,288 | A | 11/1991 | Deniega et al. |
| 5,152,754 | A | 10/1992 | Plyley et al. |

(Continued)

FOREIGN PATENT DOCUMENTS

| | | | |
|---|---|---|---|
| AU | 2007203081 A1 | 1/2008 | |
| CN | 2252603 Y | 4/1997 | |

(Continued)

OTHER PUBLICATIONS

International Application No. PCT/US21/30096, International Search Report and Written Opinion, dated Oct. 6, 2021.

(Continued)

*Primary Examiner* — Kathleen S Holwerda
*Assistant Examiner* — Daniel Icet
(74) *Attorney, Agent, or Firm* — MARSHALL, GERSTEIN & BORUN LLP

(57) ABSTRACT

A handheld body cavity access device includes a handle having a distal end, a proximal end, a longitudinal axis, and a cavity. A dilator assembly has a proximal end coupled to the handle and a distal end. A blade assembly is at least partially disposed within the dilator assembly and has a proximal end, a distal end, and a blade hub coupled to the proximal end and disposed in the cavity of the handle. The dilator assembly is movable axially between a retracted position, in which a distal end of the blade assembly extends from the distal end of the dilator assembly, and an extended position, in which the distal end of the blade assembly is covered by the distal end of the dilator assembly. The blade hub includes a body defining a bore aligned with the longitudinal axis and a tab extending away from the longitudinal axis.

6 Claims, 7 Drawing Sheets

(56) References Cited

U.S. PATENT DOCUMENTS

| | | | |
|---|---|---|---|
| 5,269,797 A | 12/1993 | Bonati et al. | |
| 5,295,977 A | 3/1994 | Cohen et al. | |
| 5,314,417 A | 5/1994 | Stephens et al. | |
| 5,320,610 A * | 6/1994 | Yoon | A61B 17/3496 |
| 5,342,382 A | 8/1994 | Brinkerhoff et al. | |
| 5,387,197 A | 2/1995 | Smith et al. | |
| 5,522,833 A | 6/1996 | Stephens et al. | |
| 5,554,137 A | 9/1996 | Young et al. | |
| 5,620,456 A | 4/1997 | Sauer et al. | |
| 5,624,459 A | 4/1997 | Kortenbach et al. | |
| 5,674,237 A | 10/1997 | Ott | |
| 5,690,664 A | 11/1997 | Sauer et al. | |
| 5,693,030 A | 12/1997 | Lee et al. | |
| 5,704,914 A | 1/1998 | Stocking et al. | |
| 5,772,678 A | 6/1998 | Thomason et al. | |
| 5,779,680 A | 7/1998 | Yoon | |
| 5,843,115 A | 12/1998 | Morejon | |
| 5,855,566 A | 1/1999 | Dunlap et al. | |
| 5,879,332 A | 3/1999 | Schwemberger et al. | |
| 5,984,941 A | 11/1999 | Wilson et al. | |
| 6,017,356 A | 1/2000 | Frederick et al. | |
| 6,056,766 A | 5/2000 | Thompson et al. | |
| 6,063,099 A | 5/2000 | Danks et al. | |
| 6,156,006 A | 12/2000 | Brosens et al. | |
| 6,402,770 B1 | 6/2002 | Jessen | |
| 6,447,527 B1 | 9/2002 | Thompson et al. | |
| 6,613,063 B1 | 9/2003 | Hunsberger | |
| D561,338 S | 2/2008 | Blanco | |
| 7,344,519 B2 | 3/2008 | Wing et al. | |
| 7,367,960 B2 | 5/2008 | Stellon et al. | |
| 7,419,496 B2 | 9/2008 | Staudner | |
| 7,731,730 B2 | 6/2010 | Popov | |
| D631,964 S | 2/2011 | Miles et al. | |
| 8,419,764 B2 | 4/2013 | Begg | |
| 8,801,741 B2 | 8/2014 | Ahlberg et al. | |
| 8,940,007 B2 | 1/2015 | Smith et al. | |
| 9,743,952 B2 | 8/2017 | Kiev | |
| 9,743,953 B2 * | 8/2017 | Kiev | A61B 17/3415 |
| 9,744,275 B2 | 8/2017 | Khouri et al. | |
| 10,588,658 B2 | 3/2020 | Kiev | |
| 10,779,857 B2 | 9/2020 | Kiev | |
| 2007/0005087 A1 * | 1/2007 | Smith | A61B 17/3417 606/185 |
| 2007/0260275 A1 | 11/2007 | Ahlberg et al. | |
| 2007/0270741 A1 | 11/2007 | Hassett et al. | |
| 2007/0270819 A1 | 11/2007 | Justis et al. | |
| 2007/0282365 A1 | 12/2007 | Popov | |
| 2008/0009894 A1 | 1/2008 | Smith | |
| 2009/0093677 A1 | 4/2009 | Smith | |
| 2009/0270896 A1 | 10/2009 | Sullivan et al. | |
| 2010/0048994 A1 | 2/2010 | Okoniewski | |
| 2011/0144678 A1 | 6/2011 | Slater | |
| 2012/0016399 A1 | 1/2012 | Poulsen | |
| 2012/0116418 A1 | 5/2012 | Belson et al. | |
| 2012/0197200 A1 | 8/2012 | Belson | |
| 2012/0221032 A1 | 8/2012 | Duperier et al. | |
| 2012/0323181 A1 | 12/2012 | Shaw et al. | |
| 2013/0123834 A1 | 5/2013 | Zook et al. | |
| 2013/0150767 A1 | 6/2013 | Tsyrulnykov et al. | |
| 2014/0135704 A1 | 5/2014 | Begg | |
| 2014/0276532 A1 | 9/2014 | Zook et al. | |
| 2015/0066056 A1 | 3/2015 | Cabrera et al. | |
| 2016/0235435 A1 | 8/2016 | Kiev et al. | |
| 2017/0290680 A1 | 10/2017 | Pinal et al. | |
| 2018/0133438 A1 | 5/2018 | Hulvershorn et al. | |
| 2018/0289391 A1 | 10/2018 | Fujii et al. | |
| 2019/0290326 A1 | 9/2019 | Zhu | |
| 2019/0307485 A1 * | 10/2019 | Kiev | A61B 17/3496 |
| 2019/0351183 A1 | 11/2019 | Ishida | |
| 2020/0170667 A1 | 6/2020 | Kiev | |
| 2020/0188634 A1 | 6/2020 | Woehr et al. | |
| 2020/0360667 A1 | 11/2020 | Aklog et al. | |
| 2020/0367928 A1 | 11/2020 | Kiev | |
| 2021/0212722 A1 | 7/2021 | Kiev et al. | |
| 2021/0259669 A1 | 8/2021 | Pattison et al. | |

FOREIGN PATENT DOCUMENTS

| | | |
|---|---|---|
| CN | 204562250 U | 8/2015 |
| CN | 105726101 A | 7/2016 |
| EP | 0135364 A2 | 3/1985 |
| EP | 2050402 B1 | 5/2011 |
| EP | 2768409 A1 | 8/2014 |
| WO | 2007/124130 A2 | 11/2007 |
| WO | 2009/010076 A1 | 1/2009 |
| WO | 2013/059175 A1 | 4/2013 |
| WO | 2014/006403 A1 | 1/2014 |
| WO | 2014/170338 A1 | 10/2014 |

OTHER PUBLICATIONS

International Application No. PCT/US21/30101, International Search Report and Written Opinion, dated Oct. 6, 2021.
International Application No. PCT/US21/30101, Invitation to Pay Additional Fees, dated Jul. 28, 2021.
U.S. Appl. No. 16/992,606, Device and Method for Access To Interior Body Regions, Filed on Aug. 13, 2020.
U.S. Appl. No. 16/782,689, Device and Method for Access to Interior Body Regions, filed Feb. 5, 2020.
International Application No. PCT/US21/30096, Invitation to Pay Additional Fees, dated Jul. 19, 2021.

* cited by examiner

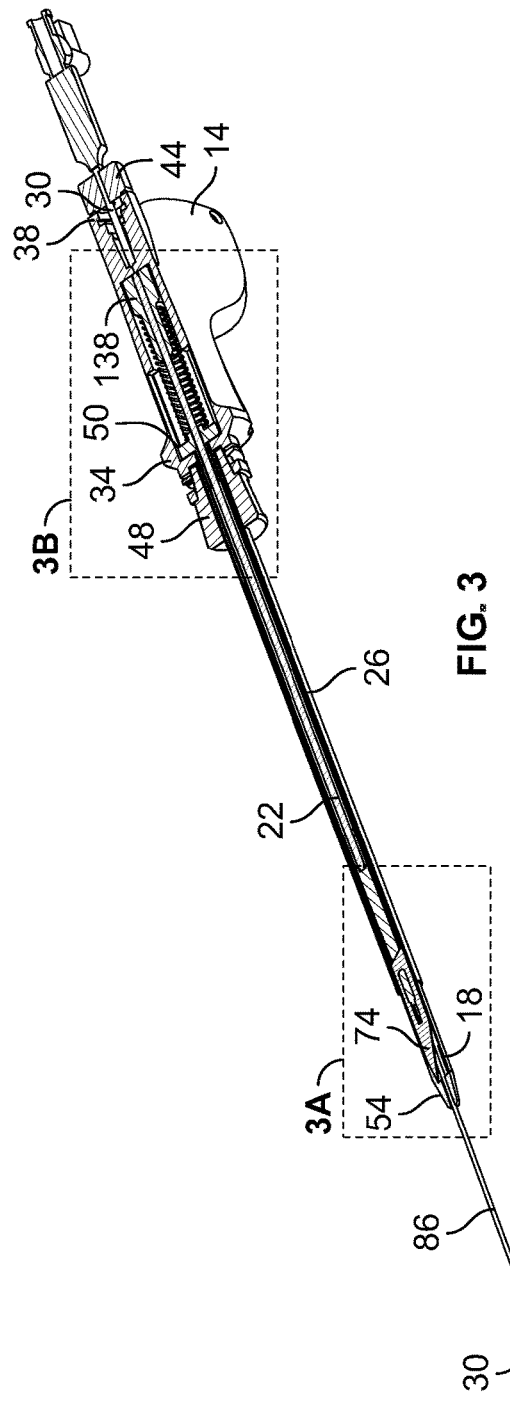
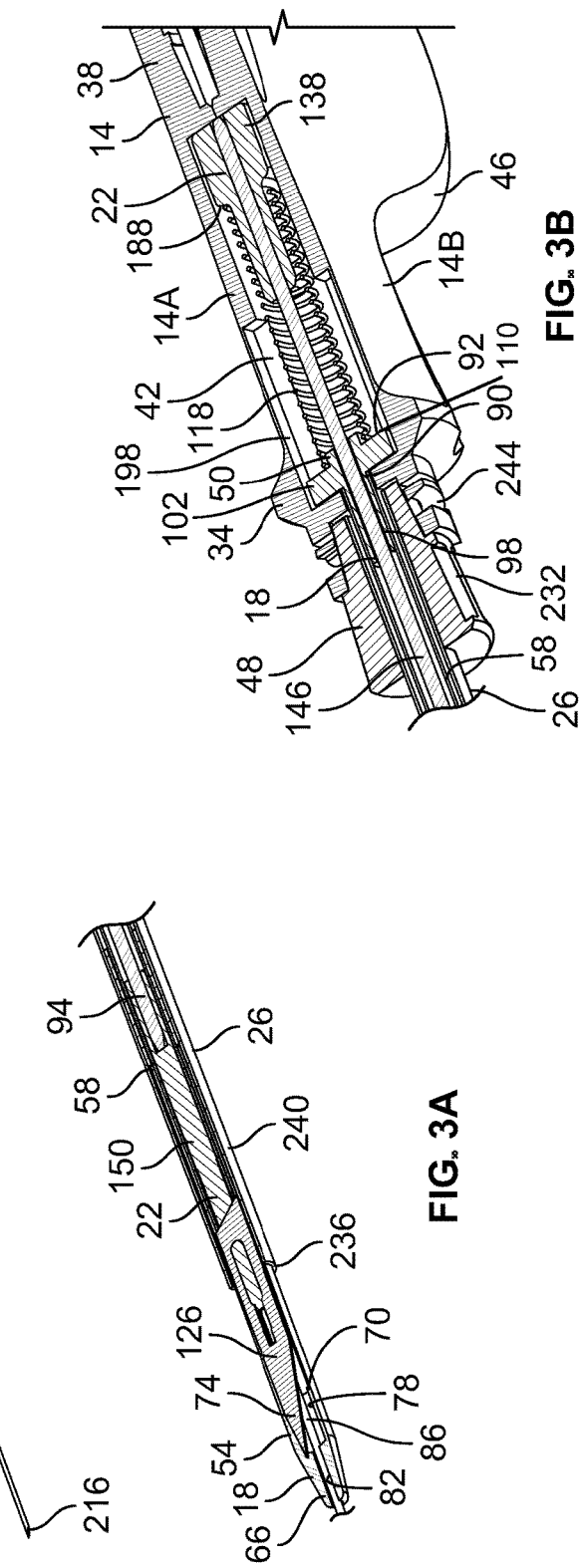

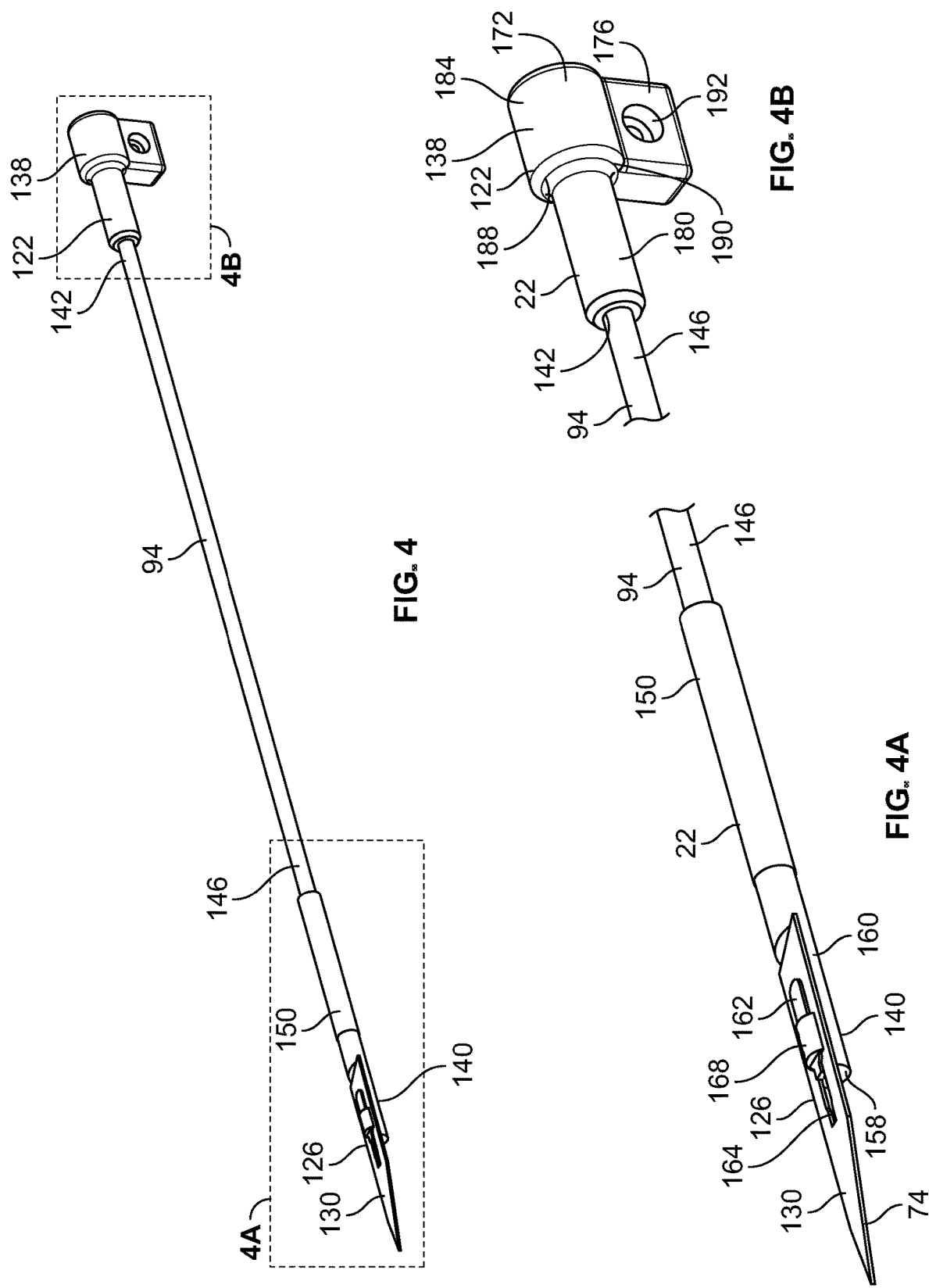

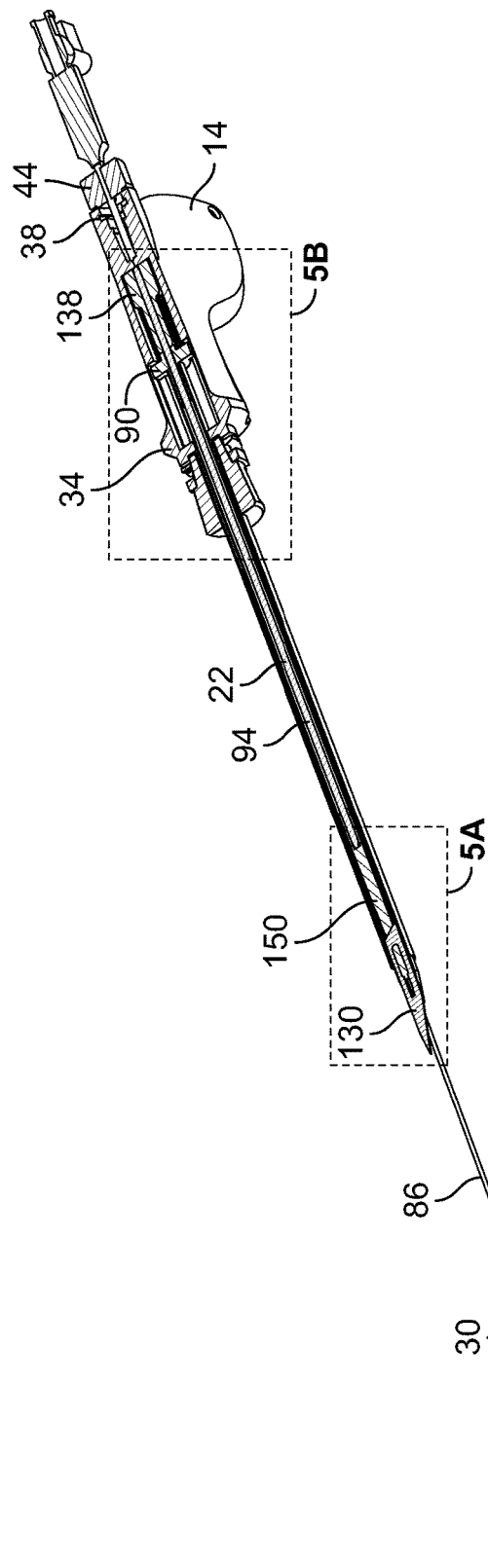
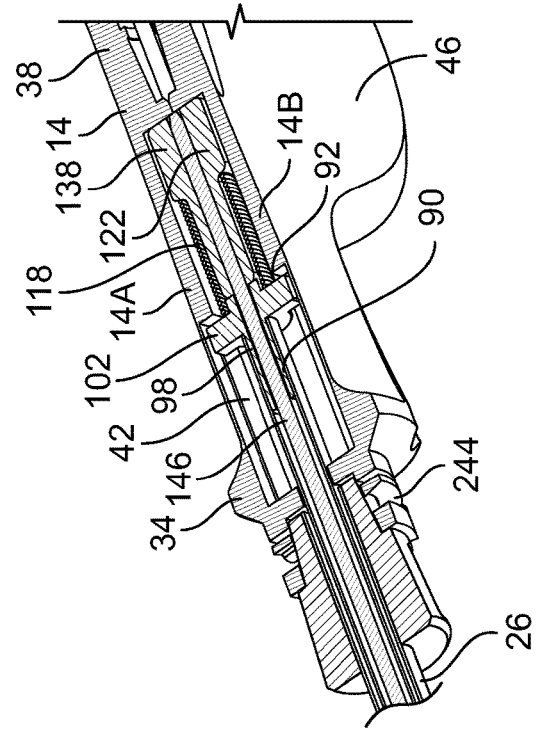
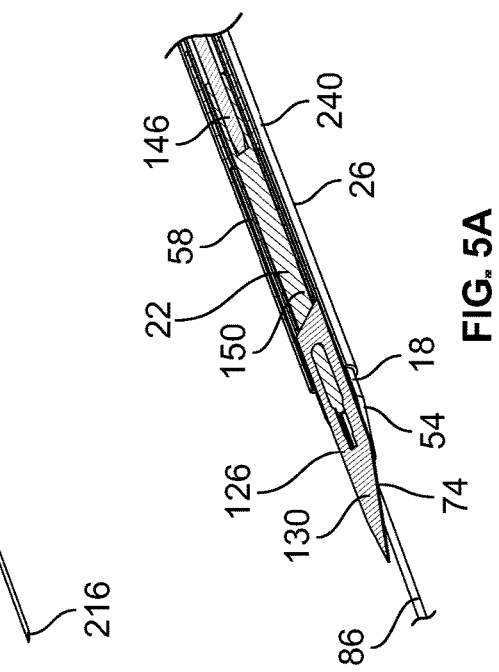
FIG. 5
FIG. 5B
FIG. 5A

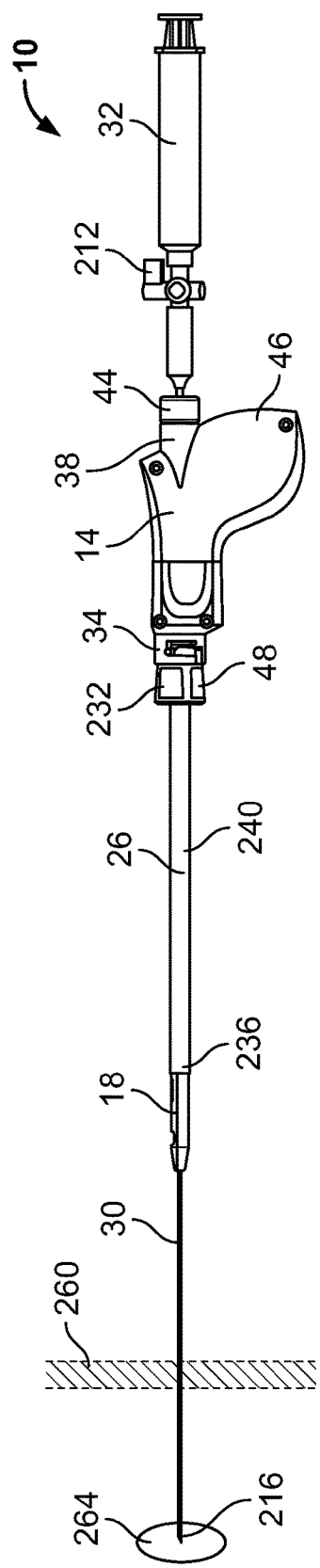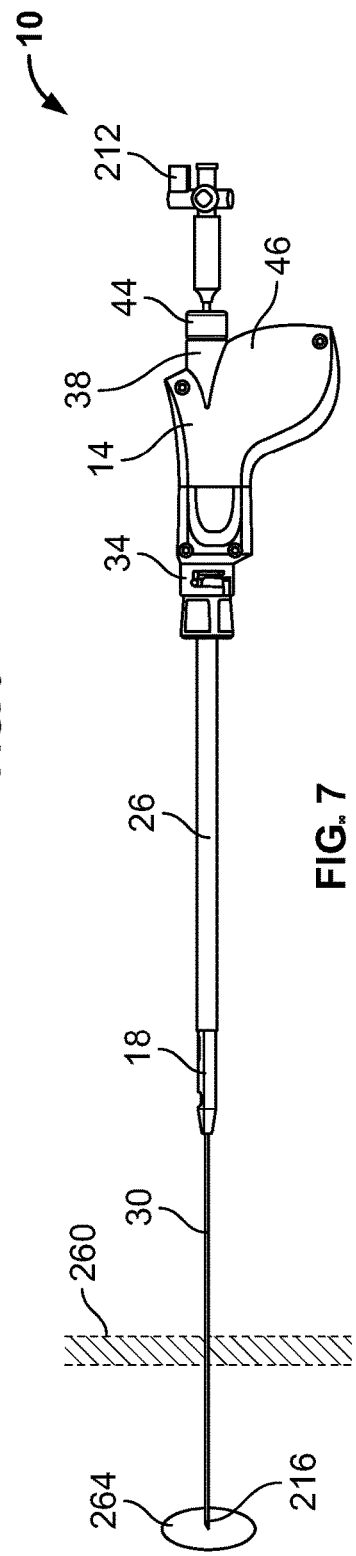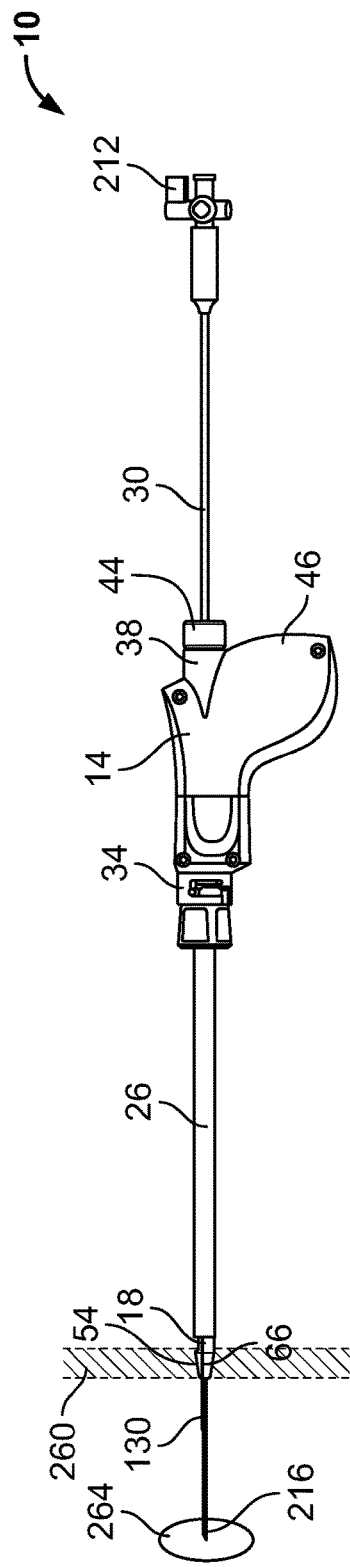

BODY CAVITY ACCESS DEVICE

FIELD OF DISCLOSURE

The present disclosure is related to a medical device, and in particular, a handheld medical device for accessing a body cavity.

BACKGROUND

In the medical field, there are many instances in which a practitioner must access the chest, abdomen, or pelvis, and insert a drainage tube. Examples of these instances include the need to relieve excess fluid in the pericardium, bleeding in the chest cavity, and fluid or air buildup in other body regions due to other medical conditions, trauma, or prior surgery.

In a traditional abdominal drain placement, for example, a practitioner must pierce the abdomen, make an incision, and insert a drain tube to drain fluid from a cyst or abscess in the abdomen. To drain the fluid, the practitioner inserts a needle through the abdominal wall and into the tissue surrounding the fluid. The practitioner may need the help of an assistant while inserting the needle to ensure that the needle is not inserted too far and nicks or pierces the surrounding organs. Typically, an ultrasound wand is placed on the patient's abdomen to follow as the needle is placed in the patient until the needle is in place of the cyst or abscess. Once the needle is in place, the practitioner will use a syringe to aspirate the fluid. After putting down the syringe, the guidewire is inserted through the needle and into the patient to the cyst or abscess. Once placed, the practitioner will make an incision with a scalpel in the area of the guidewire. The guidewire allows the advancement of multiple dilating cannulas and sheaths to sufficiently create a pathway. The dilating cannulas and sheaths are then removed and a drain is passed through to the area in question through a sheath. How was the drainage tube inserted? In this procedure, the practitioner has the needle, syringe, blade, trocar, catheter, and drainage tubes separately laid out on a table.

In other similar procedures, these steps are taken to access and drain cysts, abscesses, or other excess fluid in body cavities. If performing in the operating room, the operating doctor often requires assistance to perform the procedure because many medical instruments are used simultaneously to perform each step. These procedures can be cumbersome, involve multiple medical instruments and components, and requires coordination with multiple practitioners or healthcare providers to perform the procedures accurately and safely.

SUMMARY

In accordance with a first exemplary aspect, a handheld body cavity access device may include a handle including a distal end, a proximal end, and a longitudinal axis extending between the distal and proximal ends. The handle may have a cavity. A dilator assembly may have a proximal end coupled to the handle and a distal end spaced from the handle. A blade assembly may be at least partially disposed within the dilator assembly and may have a proximal end, a distal end, and a blade hub coupled to the proximal end and disposed in the cavity of the handle. The dilator assembly may be movable axially between a retracted position, in which a distal end of the blade assembly extends from the distal end of the dilator assembly, and an extended position, in which the distal end of the blade assembly is covered by the distal end of the dilator assembly. The blade hub may include a body defining a bore aligned with the longitudinal axis and a tab extending away from the longitudinal axis of the handle.

In accordance with a second exemplary aspect, a handheld body cavity access device may include a handle including a distal end, a proximal end, and a longitudinal axis extending between the distal and proximal ends. The handle may have a cavity aligned with the longitudinal axis. A trocar may include a proximal end coupled to the handle. A dilator assembly may be at least partially disposed within the trocar and may have a distal end. A dilator hub may be at least partially disposed in the cavity of the handle. A blade assembly may be at least partially disposed within the dilator assembly. A spring may be disposed in the cavity of the handle and biased against the dilator hub. The dilator assembly may be movable between a retracted position, in which a distal end of the blade assembly extends from the distal end of the dilator assembly and the spring is in a compressed position, and an extended position, in which the distal end of the blade assembly is covered by the distal end of the dilator assembly and the spring is in an expanded position. The spring may engage a spring seat defined by an outer surface of the dilator hub.

In accordance with a third exemplary aspect, a method of inserting a tube into a drainage site may include inserting a distal end of a needle assembly of a handheld device into a drainage site. The handheld device may include a handle including a distal end, a proximal end, and a longitudinal axis extending between the distal and proximal ends. The handle may have a cavity aligned with the longitudinal axis. A dilator assembly may have a proximal end coupled to the handle, a blade assembly at least partially disposed within the dilator assembly and having a proximal end coupled to the handle. The method may include receiving a force on a distal end of the dilator assembly. The force may compress a spring to move the dilator assembly to a retracted position, in which a distal end of the blade assembly extends from the distal end of the dilator assembly. The spring may be disposed in the cavity of the handle between the blade assembly and the dilator assembly. Further, the method may include decoupling the needle assembly from the handle such that the handle moves relative to the needle assembly, and inserting a distal end of the trocar assembly into the drainage site. Finally, the method may include decoupling a proximal end of the trocar assembly from the handle such that the handle moves axially relative to the trocar assembly, and removing the handle from the trocar assembly.

In accordance with a fourth exemplary aspect, a handheld body cavity access device may include a handle having a distal end, a proximal end, and a longitudinal axis extending between the distal and proximal ends. The handle may include a cavity, a first opening at the proximal end, a second opening at the distal end, and a pathway connecting the first and second openings. A needle assembly may be at least partially disposed in the handle and movable relative to the handle. The needle assembly may include a conduit aligned with the longitudinal axis of the handle and disposed in the pathway of the handle. A trocar assembly may include hub and a trocar tube. The hub may be disposed at a proximal end of the tube and removably coupled to the distal end of the handle. A dilator assembly may include a shaft, a dilator hub, and a biasing element. The shaft may be at least partially disposed within the trocar tube and may have a proximal end coupled to the handle and a tapered distal end extending from a distal end of the trocar tube. The distal end of the shaft may have a slot, and the proximal end of the shaft may be coupled to the dilator hub disposed in the cavity of the handle. The biasing element may be in a biasing engagement with a spring seat of the hub. A blade assembly may be at least partially disposed within the shaft and movable through the slot in the distal end of the trocar tube. The blade assembly may include a blade and a blade guide. The blade guide may include a distal end coupled to the blade and extending through the trocar and the cavity of the handle. A proximal end of the blade guide may be fixed to the handle. A rotatable lock may be coupled to the proximal end of the handle. The lock may be movable between an unlocked position, in which the needle assembly is movable relative to the handle, and a locked position, in which the needle assembly is fixed to the handle assembly. The biasing element of the dilator assembly may be disposed in the cavity of the handle between the spring seat of the dilator assembly and the proximal end of the blade guide. The biasing element may be movable between a compressed position, in which the blade is disposed through the slot of the trocar tube and an expanded position, in which the blade is covered by the dilator assembly.

In further accordance with any one or more of the foregoing first, second, third, and fourth aspects, a handheld body cavity access device and method for inserting a tube into a drainage site may further include any one or more of the following preferred forms.

In a preferred form, a spring may be disposed in the cavity of the handle and biased between the proximal end of the dilator assembly and the body of the blade hub.

In a preferred form, the spring may at least partially surround a portion of the blade hub.

In a preferred form, the blade assembly may include a blade and a hollow tube coupled to the blade.

In a preferred form, the hollow tube may include a distal end disposed in the bore of the blade hub.

In a preferred form, the blade assembly may includes a cap coupled to a proximal end of the hollow tube.

In a preferred form, the blade may be mounted to the cap.

In a preferred form, the proximal end of the dilator assembly may include a dilator hub defining a spring seat engaging a distal end of the spring.

In a preferred form, the dilator hub may have a symmetrical cross-section about the longitudinal axis.

In a preferred form, the dilator hub may include an outer surface defining the spring seat.

In a preferred form, the dilator assembly may include a shaft having a bore and a tapered distal end.

In a preferred form, the dilator hub may be at least partially disposed in the bore of the shaft at a proximal end of the shaft.

In a preferred form, a needle assembly may be at least partially disposed in the handle and movable relative to the handle.

In a preferred form, the needle assembly may include a conduit aligned with the longitudinal axis of the handle.

In a preferred form, the needle assembly may be coupled to the handle by a lock so that when the needle assembly is in a locked position, the needle and handle are movable together.

In a preferred form, when the needle assembly is in an unlocked position, the handle may be movable relative to the needle.

In a preferred form, the needle assembly may be slidably coupled to the proximal end of the handle by a lock.

In a preferred form, a trocar may include a proximal end coupled to the handle.

In a preferred form, the dilator assembly may be at least partially disposed in the trocar.

In a preferred form, the distal end of the dilator assembly may extend from a distal end of the trocar.

In a preferred form, the tab of the blade hub may be adjacent to an inner wall of the handle.

In a preferred form, the dilator hub may have a symmetrical cross-section about the longitudinal axis.

In a preferred form, the dilator assembly may include a shaft having a bore and a tapered portion at the distal end.

In a preferred form, the dilator hub may be at least partially disposed in the bore of the shaft at a proximal end of the shaft.

In a preferred form, the blade assembly may include a blade hub disposed in the cavity of the handle.

In a preferred from, the blade hub may have a body defining a bore aligned with the longitudinal axis and a tab extending away from the longitudinal axis of the handle.

In a preferred form, the spring may engage the spring seat of the dilator hub.

In a preferred form, a spring seat may be defined by the body of the blade hub.

In a preferred form, the spring may at least partially surround a portion of the blade hub.

In a preferred form, the blade assembly may include a blade and a hollow tube carrying the blade.

In a preferred form, the hollow tube may include a distal end disposed in the bore of the blade hub.

In a preferred form, the tab of the blade hub may be adjacent to an inner wall of the handle.

In a preferred form, the conduit of the needle assembly may extend through a bore of the blade assembly In a preferred form, the dilator hub may include an annular ring separating a proximal end of the cavity of the handle and a proximal end of the spring.

In a preferred form, a syringe may be removably coupled to a valve of the needle assembly.

In a preferred form, the method may include drawing fluid from the drainage site using a syringe coupled to a proximal end of the needle assembly.

In a preferred form, the method may include opening a valve coupled to the needle assembly before drawing fluid from the drainage site.

In a preferred form, the method may include decoupling the syringe from the needle assembly after drawing fluid into the syringe.

In a preferred form, the method may include closing the valve coupled to the needle assembly before decoupling the syringe.

In a preferred form, removing the trocar assembly from the handle may include sliding the dilator assembly and blade assembly relative to the trocar assembly.

In a preferred form, the method may include inserting a drain tube into a bore of the trocar assembly.

In a preferred form, the method may include removing the trocar assembly from the drainage site.

In a preferred form, decoupling the needle assembly may include rotating a lock of the handle to disengage the handle from the needle assembly.

In a preferred form, the method may include locking the needle assembly to the handle before removing the handle from the trocar assembly.

BRIEF DESCRIPTION OF THE DRAWINGS

FIG. 3 is a top perspective, cross-sectional view of the device of FIG. 1, showing the device in an initial configuration;

FIG. 3A is a magnified, cross-sectional view of the device of FIG. 3, showing a distal portion of a dilator assembly and a blade assembly;

FIG. 3B is a different magnified, cross-sectional view of the device of FIG. 3, showing a proximal portion of the dilator assembly and the blade assembly;

FIG. 4 is a top perspective view of the blade assembly of FIG. 2;

FIG. 4A is a magnified, perspective view of a distal end of the blade assembly of FIG. 4;

FIG. 4B is a magnified, perspective view of a proximal end of the blade assembly of FIG. 4;

FIG. 5 is a top perspective, cross-sectional view of the device of FIG. 1, showing a blade of the blade assembly exposed when the device is in an advanced position;

FIG. 5A is a magnified, cross-sectional view of the device of FIG. 5, showing the distal portion of the dilator assembly and the blade assembly;

FIG. 5B is a different magnified, cross-sectional view of the device of FIG. 5, showing the proximal portion of the dilator assembly and the blade assembly;

FIG. 6 is a side view of the device of FIG. 1, showing the device in an insertion position with the syringe attached;

FIG. 7 is a side view of the device of FIG. 1, showing the device in the insertion position with the syringe detached;

FIG. 8 is a side view of the device of FIG. 1, showing the device in the advanced position;

DETAILED DESCRIPTION

Figure 1:
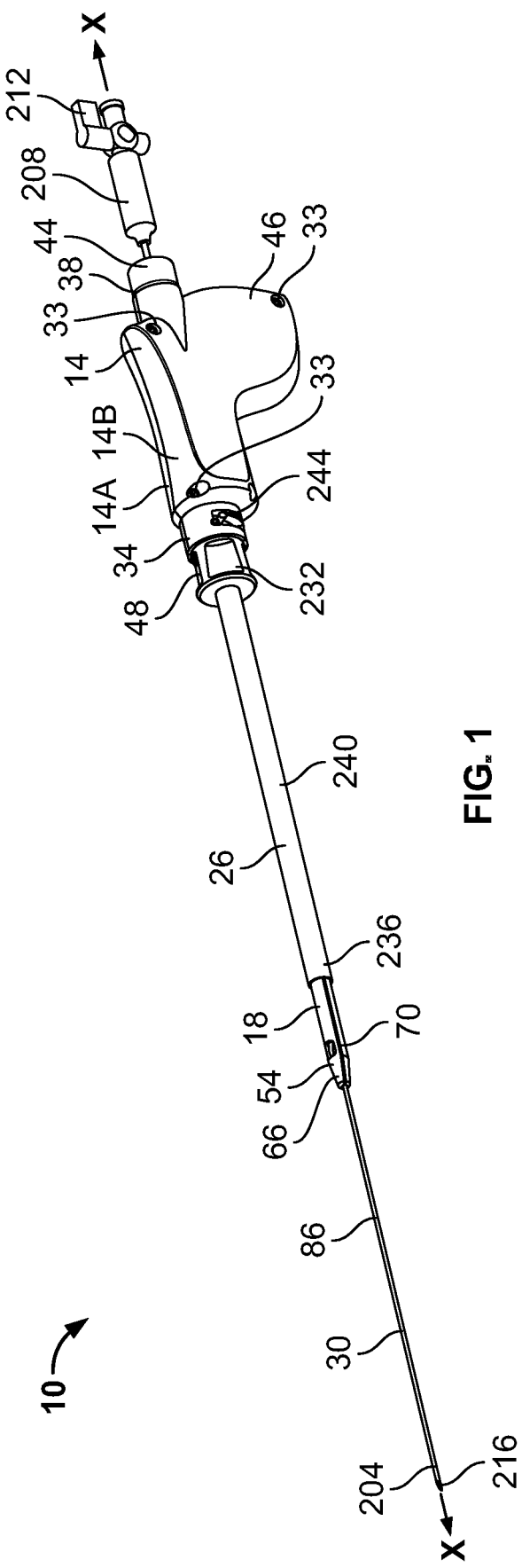
FIG. 1 is a side, perspective view of a handheld body cavity access device assembled in accordance with the teachings of the present disclosure, and showing the device in a loaded configuration.

In FIG. 1, a handheld body cavity access device 10 for rapid percutaneous drain placement in abdomen, pelvis, or other body part is constructed in accordance with the teachings of the present disclosure. The disclosed device provides a user the ability to perform multiple functions of a surgical procedure that is typically performed with assistance from at least one other medical professional. For example, a user of the device 10 can access a body cavity, drain a fluid from the body cavity, and install a drain tube into the body cavity of a patient.

Figure 2:
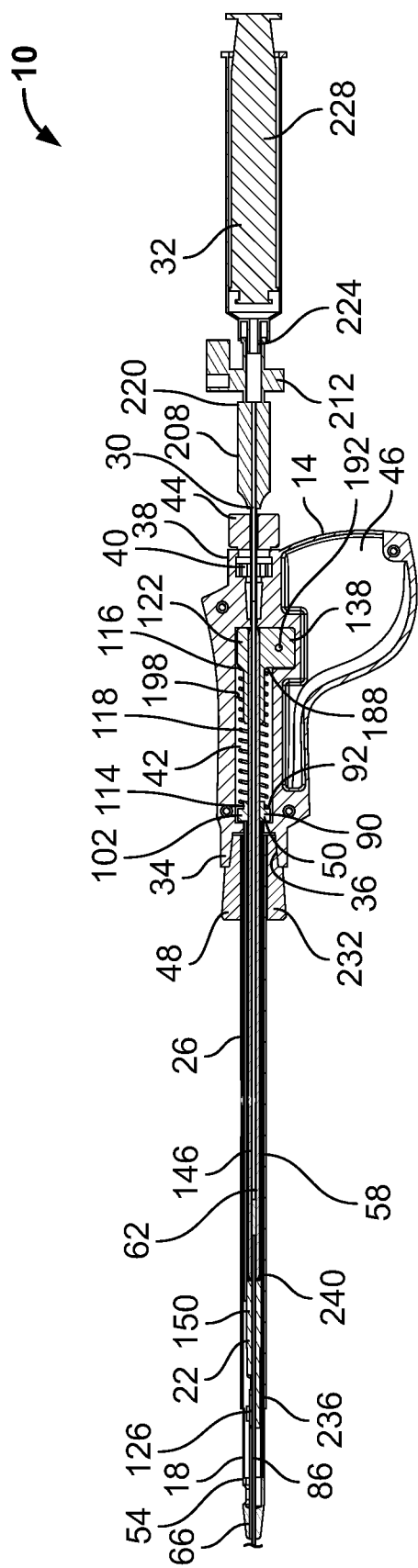
FIG. 2 is a side cross-sectional view of the device of FIG. 1, showing the device connected to a syringe.

In FIGS. 1 and 2, the device 10 includes a handle 14, a dilator assembly 18, a blade assembly 22 (FIG. 2), a trocar 26, and a needle assembly 30. To operate the device 10, a user grips the handle 14 and inserts a distal pointed tip of the needle assembly 30 into a drainage site. As shown in FIG. 2, a syringe 32 is coupled to the needle assembly 30 and is used to collect a fluid sample from the drainage site. After a sample is collected and the syringe 32 is removed from the device 10, the needle assembly 30 is unlocked from the handle 14 and the device 10 is pushed further into a body of the patient. The skin and flesh of the patient apply a resistive force against the dilator assembly 18, thereby pushing the dilator assembly 18 toward the handle 14 and exposing the blade assembly 22. The blade assembly 22 cuts through the tough body tissue until the dilator assembly 18 re-covers the blade assembly 22 so that the device can further enter into the patient safely. When the dilator assembly 18 reaches the drainage site, the trocar 26 is unlocked from the handle 14 and remains inside the patient as the handle 14, which carries the needle assembly 30, blade assembly 22, and dilator assembly 18, is removed from the patient. The trocar 26 remains in place to provide an opening until a user inserts a drainage tube into the drainage site.

The handle 14 is a housing of the movable components and assemblies of the device 10, and includes a distal end 34, a proximal end 38, and a longitudinal axis X extending between the distal and proximal ends 34, 38. The handle 14 includes a cavity 42 aligned with the longitudinal axis X and arranged to at least partially receive the dilator assembly 18, the blade assembly 22, and the needle assembly 30. A hollow grip 46 is spaced away from the cavity 42 and the longitudinal axis X and is shaped to fit comfortably and securely within a palm of a user's hand. The grip 46 of the handle 14 may be shaped differently or may include gripping features to improve a user's grip and operation of the device 10. This may include dimples, grooves, corrugations, rubberized features, etc.

In the illustrated example of FIG. 1, the handle 14 includes first and second halves 14A, 14B secured together with a plurality of fasteners 33. When the first and second halves 14A, 14B are coupled, the handle 14 defines a first opening 36 at the distal end 34, a second opening 40 at the proximal end 38, and a central bore that connects the first opening 36, second opening 40, and cavity 42. At the first opening 36, the handle 14 receives the needle assembly 30 and includes a lock 44 that couples the needle assembly 30 to the handle 14. At the second opening 40, the handle 14 receives a locking hub 48 of the trocar 26. This clam-shell configuration of the handle 14 facilitates loading the handle 14 with the various components and assemblies of the device 10. However, in other examples, the handle 14 may be constructed and fastened together differently.

Turning to FIGS. 2 and 3, the dilator assembly 18 includes a proximal end 50 coupled to the handle 14, a distal end 54 spaced from the handle 14, and a shaft 58 extending between the proximal and distal ends 50, 54 of the dilator assembly 18. The shaft 58 is cylindrical and includes a bore 62 that is sized to receive at least a portion the blade assembly 22. In FIG. 3A, the distal end of 54 of the dilator assembly 18 includes a tapered end 66 extending from a distal end 236 of the trocar 26. The tapered end 66 defines a lateral slot 70, parallel with the longitudinal axis X, and sized to slidably receive a blade edge 74 of the blade assembly 22. The tapered end 66 is coupled to a distal end of the shaft 58 and includes a bore that is continuous with the bore 62 of the shaft 58. However, the bore of the tapered end 66 includes two different-sized bores: a first bore 78 sized and shaped to receive the blade edge 74 of the blade assembly 22, and a more narrow second bore 82 sized to receive a conduit 86 of the needle assembly 30.

As shown in FIG. 3B, the proximal end 50 of the dilator assembly 18 includes a dilator hub 90 defining a spring seat 92. The dilator hub 90 is coupled to a proximal end of the shaft 58 and is at least partially disposed in the cavity 42 of the handle 14. The hub 90 is hollow to slidably receive a blade guide 94 of the blade assembly 22, and includes a tubular portion 98 and a flange 102 extending radially outward from the tubular portion 98. The tubular portion 98 of the dilator hub 90 is at least partially disposed in the bore 62 of the shaft 58 and is securely coupled to the shaft 58 by friction fit. As shown in an initial configuration in FIG. 3B, the tubular portion 98 of the hub 90 extends through the first opening 36 in the distal end 34 of the handle 14 and the flange 102 engages an interior wall 198 defining the cavity 42. On an opposite outer surface 110 of the flange 102, the hub 90 defines the spring seat 92, which engages a distal end 114 of a spring 118. In the illustrated example, the dilator hub 90 has a symmetrical cross-section about the longitudinal axis X. However, in other examples, the hub 90 may be asymmetrical or otherwise shaped differently to both connect with the shaft 58 and define the spring seat 92 for the spring 118.

Turning briefly back to FIG. 1, the blade assembly 22 is completely shielded by the dilator assembly 18 and handle 14 when the device 10 is in an initial position. FIGS. 3, 3A, 3B depict how the blade assembly 22 is arranged around the needle assembly 30 and within the dilator assembly 18 and partially within the handle 14. Turning now to FIGS. 4, 4A, and 4B, the blade assembly 22 is isolated from the other components of the device 10, and includes a proximal end 122, a distal end 126, a blade 130, the blade guide 94 carrying the blade 130, and a blade hub 138 opposite the blade 130. The blade guide 94 includes a distal end 140 coupled to the blade 130 and a proximal end 142 coupled to the blade hub 138.

In FIGS. 4 and 4A, the distal end 126 of the blade assembly 22 is shown in more detail. At the distal end 126, the blade guide 94 includes a hollow tube 146 and a cap 150 coupling the hollow tube 146 to the blade 130. The hollow tube 146 of the blade assembly 22 is axially aligned with the longitudinal axis X of the device 10 and includes a bore sized to receive the conduit 86 of the needle assembly 30. In this way, the tube 146 provides a guide for the conduit 86 from the proximal end 38 of the handle 14 to the distal end 126 of the blade assembly 22. The cap 150 is coupled to a distal end of the tube 146 and includes a larger diameter to mount the blade 130 to the hollow tube 146. The hollow tube 146 and the cap 150 of the blade guide 94 are separate components, however, in another exemplary blade assembly, the blade guide 94 is an integrated component.

In FIG. 4A, a distal end 158 of the cap 150 includes a flat portion 160 cut-out from the tubular shape of the cap 150 and a protrusion 162 extending from the flat portion 160 and into an opening 164 of the blade 130. A fastener 168 couples the blade 130 to the cap 150 by clamping the protrusion 162 between the fastener 168 and blade 130. In this arrangement, the fastener 168 may be removed to replace the blade 130 easily and secure a blade of a different size or shape to the cap 150 of the blade assembly 22 before the device 10 is fully assembled, based on the application of the device 10. However, in other examples, the blade 130 may not be removably replaced from the blade guide 94 and may be arranged differently to secure the blade guide 94 to the blade 130.

In FIG. 4B, the proximal end 122 of the blade assembly 22 is shown in more detail. The blade hub 138 includes a body 172 and a tab 176. The body 172 of the blade hub 138 defines a bore aligned with the longitudinal axis X and is sized to receive the proximal end of the tube 146. The body 172 includes a first cylindrical portion 180 that receives the hollow tube 146 and a second cylindrical portion 184 coupled to the tab 176 and defining a spring seat 188 in an outer surface 190. The tab 176 extends away from the longitudinal axis X and includes an aperture 192 extending perpendicularly relative to the longitudinal axis X. The aperture 192 is sized to receive a fastener to fixedly attach the tab 176, and therefore the blade hub 138, to an inner wall 198 of the cavity 42, as shown in FIG. 2. As such, the blade assembly 22 is fixed to the handle 14 of the device 10 and therefore does not move relative to the handle 14.

The spring 118 is disposed in the cavity 42 of the handle 14 between the proximal end 50 of the dilator assembly 18 and the distal end 126 of the blade assembly 22. In particular, the spring 118 is a coil spring with the distal end 114 engaging the dilator hub 90, and a proximal end 116 engaging the spring seat 188 of the blade hub 138. However, in other examples, the spring 118 may be a different biasing element or device that provides a biasing or resistant force to the dilator hub 90. For example, the biasing device 118 may be a flexible member, pressurized gas, or other methods and devices for generating a force. The spring 118 is movable between a compressed position, in which the blade 130 is disposed through the lateral slot 70 of the trocar 26 and an expanded position, in which the blade 130 is covered by the dilator assembly 18. The spring 118 at least partially surrounds a portion of the blade hub 138, and in particular, the first cylindrical portion 180 of the body 172. The spring 118 may have a spring constant in a range between approximately 0.5 lbs/inch to approximately 1.25 lbs/inch, and a particular spring constant may be determined based on the location of the distal end 54 of the dilator assembly 18 relative to the blade edge 74 of the blade assembly 22. In one exemplary arrangement, the spring 118 has a spring constant of approximately 0.76 lbs/inch.

Turning back to FIGS. 1 and 2, the needle assembly 30 is at least partially disposed in the handle 14 and movable relative to the handle 14. The needle assembly 30 includes the conduit 86, a distal end 204, a proximal end 208, and a valve 212. At the distal end 204, the conduit 86 includes a sharp distal tip 216 (FIG. 1) that extends beyond the distal end 54 of the dilator assembly 18 and a proximal end 220 (FIG. 2) that couples to the valve 212. At the proximal end 220, the valve 212 is disposed outside of the proximal end 38 of the handle 14 and is in fluid communication with the conduit 86. In particular, the proximal end 220 of the conduit 86 extends into an interior bore of the valve 212 and is in fluid communication with an interior flow path of the valve 212.

In the initial position shown in FIGS. 1 and 2, the conduit 86 is aligned with the longitudinal axis X of the handle 14 and extends from the valve 212 through a bore in the lock 44 and the second opening 40 in the handle 14, through each of the blade and dilator assemblies 22, 18 and the cavity 42 of the handle 14, and out the distal end 54 of the dilator assembly 18. As shown in FIG. 2, the syringe 32 is coupled to a port 224 of the valve 212 opposite the proximal end 220 of the conduit 86. A distal end 208 of the syringe 32 is in fluid communication with the valve port 224 such that when the valve 212 is in an open position, an operator can draw fluid through the needle assembly 30 and into a reservoir 228 of the syringe 32. As will be described further below, the valve 212 may be closed and the syringe 32 can be removed from the device 10.

The needle assembly 30 is slidably coupled to the handle 14 by the rotatable lock 44 at the proximal end 54 of the handle 14. The lock 44 is arranged to engage an outer circumference of the conduit 86 to prevent relative movement of the needle assembly 30 and the handle 14 when the lock is in a locked configuration. In particular, the lock 44 includes an elastomer seal disposed around the conduit 86 of the needle assembly 30. When the lock 44 is in the locked position, the lock 44 squeezes the elastomer seal around the conduit 86, thereby locking the needle assembly 30 to the handle 14. In this configuration, the needle assembly 30 and handle 14 are movable together. In an unlocked position, the lock 44 releases the elastomer seal to permit the needle assembly 30 to slide relative to the handle 14. As such, the handle 14 is movable relative to the needle assembly 30.

In FIG. 1, the trocar 26 is coupled to the first opening 36 at the proximal end 38 of the handle 14. The trocar 26 includes a proximal end 232 coupled to the handle 14, a distal end 236 opposite the proximal end 232, a tube 240, and the locking hub 48. The tube 240 includes an inner diameter large enough to at least partially receive the dilator assembly 18. As shown in FIGS. 1-2, the distal end 54 of the dilator assembly 18 extends beyond the distal end 236 of the trocar 26. At the proximal end 232 of the trocar 26, the hub 48 is coupled to the distal end 34 of the handle 14 and is at least partially disposed in the first opening 36 of the handle 14. As shown in FIG. 1, the distal end 34 of the handle 14 includes a channel 244 that receives a pin extending from the trocar locking hub 48 and into the channel 244 of the handle 14. The locking hub 48 is rotatably coupled to the distal end 34 of the handle 14 by engaging the pin of the locking hub 48 in the channel 224 of the handle 14. The locking hub 48 and the handle 14 may be coupled by other or additional means, such as, for example, internal and external threads to releasably engage the trocar 26 from the handle 14. As will be described further below, the trocar 26 may be unlocked and separated from the distal end 34 of the handle 14 to create a conduit 86 for drain tube placement into a patient.

The movement of the dilator assembly 18 when the device 10 is in the initial and advanced configurations is illustrated in FIGS. 3 and 5, respectively. In the initial position shown in FIGS. 3, 3A, and 3B, the distal end 126 of the blade assembly 22 is covered by the distal end 54 of the dilator assembly 18, and the spring 118 is in an expanded position. In the expanded position, the spring 118 biases the dilator hub 90 against the interior wall 198 of the distal end of the cavity 42 of the handle 14. In the advanced position shown in FIGS. 5, 5A, and 5B, the dilator assembly 18 is in a retracted position, in which the distal end 126 of the blade assembly 22 extends from the distal end 54 of the dilator assembly 18. The dilator hub 90 compresses the spring 118 and moves in a direction toward the proximal end 38 of the handle 14 and the blade hub 138. Movement of the dilator hub 90 carries the dilator assembly 18 so that that the distal end 54 slides over the blade edge 74 of the blade 130, thereby exposing the blade 130. In other words, movement of the dilator assembly 18 exposes the blade assembly 22 by permitting the blade 130 to slide through the slot 70 in the distal end 54 of the dilator assembly 18. As the dilator assembly 18 moves between these two positions, the handle 14 and the blade assembly 30 do not move.

Operating the device of FIGS. 1-5B will be described with reference to FIGS. 6-10. Initially, a medical practitioner (i.e., the operator) identifies a pelvic or abdominal area in a patient that requires drainage. The skin is prepped, draped and anesthetized before using the device 10. Using monitoring equipment and image guidance, the operator inserts the device 10 through skin tissue 260 of the patient by piercing the patient with the sharp tip 216 of the needle assembly 30, and inserting the needle assembly 30 into a body cavity 264 that requires draining. In FIG. 6, the device 10 is in a sample collection position. To aspirate the body cavity 264 for a fluid sample, the operator opens the valve 212 and draws fluid disposed in the cavity 264 through the conduit 86 of the needle assembly 30 and into the reservoir 228 of the syringe 32. The operator then closes the valve 212, for example, by rotating a lever, and removes the syringe 32 from the needle assembly 30 of the device 10. The sample of the aspirated fluid may be sent for culture or cytological analysis. FIG. 7 illustrates the device 10 in the initial position (as shown in FIGS. 3, 3A, 3B) with the syringe 32 removed. Before inserting the device 10 further into the patient, the operator rotates the lock 44 to disengage the handle 14 from the needle assembly 30 so that the handle 14 carrying the trocar 26, blade assembly 22, and dilator assembly 18 can move relatively to the needle assembly 30.

FIG. 8 illustrates the device 10 in the advanced position (as shown in FIGS. 5, 5A, 5B). The distal end 216 of the needle assembly 30 remains in place in the body cavity 264 of the patient as the device 10 moves further into the patient toward the distal end 216 of the needle assembly 30. The needle assembly 30 does not move relative to the handle 14 as the device 10 advances. As the operator guides the device 10 into the patient, the body tissue 260 of the patient apply a force to the distal end 54 of the dilator assembly 18, causing the dilator assembly 18 to slide relative to the blade assembly 22 and expose edge 74 of the blade 130. The blade 130 cuts through the body tissue 260 to make an incision and the tapered end 66 of the dilator assembly 18 gently guides the device 10 through the incision and to the body cavity 264. After the device 10 pierces through the tough body tissue 260 of the patient, the spring force of the spring 118 overcomes the resistive force of the body tissue 264 against the distal end 54 of the dilator assembly 18, thereby returning the dilator assembly 18 to the initial position and covering the distal end 126 of the blade assembly 22. In this way, the blade 130 is only exposed when an incision is needed, and then is automatically covered to protect the patient when the incision is made and the device 10 further advances into the body of the patient. The device 10 is in place when the distal end 236 of the trocar 26 is disposed in the cavity 264 of the patient.

Figure 9:
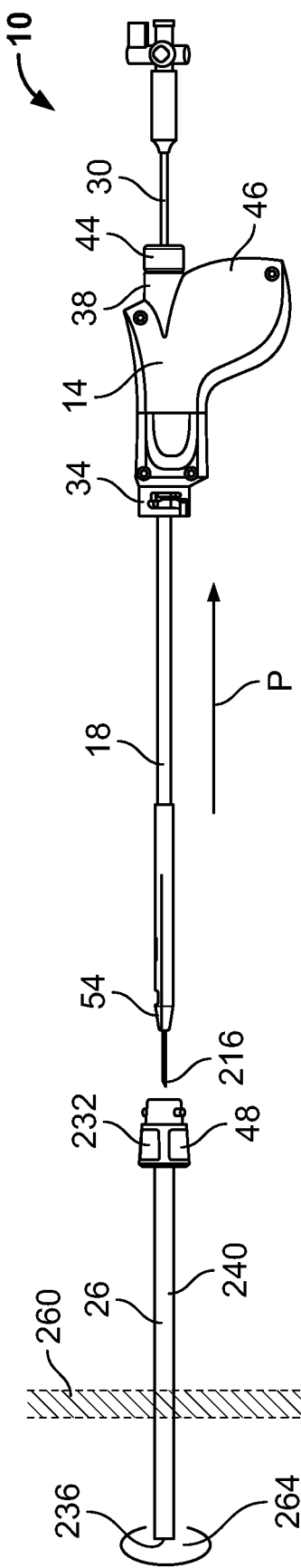
FIG. 9 is a side view of the device of FIG. 1, showing a trocar of the device in a drainage site.
Figure 10:
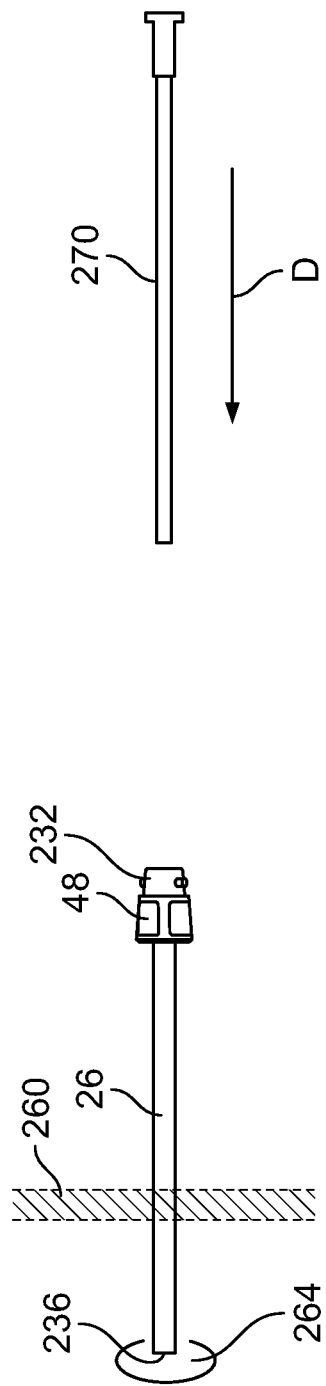
FIG. 10 is a side view of a drain adjacent to the trocar for placement in the drainage site.

In FIG. 9, the trocar 26 remains in the patient as the device 10 is removed. To remove the device 10 from the patient and from the trocar 26, the operator rotates the lock 44 to engage the needle assembly 30 so that the needle assembly 30 is once again locked to the handle 14 (and therefore moves with the handle 14). Then the operator rotates the locking hub 48 from the distal end 34 of the handle 14 to remove the trocar 26 from the handle 14. The operator then slides the device 10 away from the trocar 26 in a P direction, thereby removing the needle, blade, and dilator assemblies 30, 22, 18 from the patient. As shown in FIG. 10, the trocar 26 is disposed in the drainage site of the patient and is in position to receive a draining tube 270. The operator inserts the draining tube 270 into the bore of the trocar 26 by moving the draining tube 270 in a D direction. Once the draining tube 270 is in place, the trocar 26 may be removed from the patient by sliding the trocar over the draining tube 270, leaving the draining tube 270 inside the patient. Finally, the operator sutures the incision site and a drain bag is attached to the drain tube.

The exemplary body cavity device 10 provides all the instrumentation and components for rapid percutaneous drain placement in an abdomen or pelvis of a patient. The device 10 permits a single operator to perform a procedure that may require two people to perform. While holding the device 10 in one hand, the operator can insert the needle assembly 30 into a drainage site of a patient, aspirate fluid from the drainage site by drawing in fluid with the syringe 32, make an incision with the blade assembly 22, detach the trocar from the handle 14 of the device 10, and remove the dilator, blade, and needle assemblies 18, 22, 30 from the patient. To perform this type of procedure, for example, the practitioner no longer needs to access each individual instrument laid out on a separate table. Further, the practitioner is free to use their second hand to operate an ultrasound wand while applying the device 10 in their other hand.

The device 10 handle 14 itself is simply constructed and operated. An operator may hold the device 10 in one hand, and operate the lock 44, syringe 32, and trocar hub 48 with another to perform each step of the medical procedure. The handle 14 simply houses the spring 118 and protects the movement of the dilator and blade assemblies 18, 22 between the initial and advanced positions. In this way, the device 10 has a compact design, is simply constructed, and protects its moving components.

The device 10 may provide a safer method that involves less risk for guiding a needle assembly 30 and making an incision with a blade 130. With a rotatable lock 44, the operator can couple and decouple the needle assembly 30 from the handle 14 with ease. Once the needle assembly 30 is in place in the cavity 264 of the patient, the operator can easily slide the handle 14 relative to the needle assembly 30 without worry of further plunging the sharp tip 216 of the needle assembly 30 into the patient. Additionally, the dilator and blade assemblies 18, 22 work together to automatically cover, expose, and recover the blade 130 of the blade assembly 22 to make an incision only when needed. Rather than making an incision with a separate device, the handheld device 10 of the present disclosure responds to the resistive force of the patient's body to expose the blade assembly 22 to make the incision. Once the incision is made, the dilator assembly 18 automatically returns to its initial position to cover the blade 22 from inadvertent nicks or pierces of the blade 130 within the patient.

Additionally, the disclosed device 10 obviates the need for using suing a guidewire to guide the needle assembly 30 to the correct drainage site. Rather than thread a guidewire through the device, which is very long and delicate, the needle assembly 30 of the disclosed device 10 acts as the guide for the device 10 as the blade 130 makes the incision to reach the area requiring drainage.

The disclosed device 10 may be used in many different medical procedures to access different body cavities of a patient. The device 10 may be used to drain a cavity of excess fluid, or, in other applications, the device 10 may be used to inject a patient with a medicine via the syringe 32. While the disclosed exemplary device 10 is intended for single-use, in some applications, the device 10 may be sterilized and reused. Additionally, the device 10 may include different fittings or adapters, for example, a syringe adapter, to receive different models or types of syringes. In another example, the spring 118 may be replaced with a spring having a different spring constant, depending on the application of the device. For example, the resistive force of body tissue may be different for an elderly patient, and therefore a spring with a lower spring constant may be desired. In another example, the blade 130 may be replaced to create a smaller incision, for example.

Additive Manufacturing Technology may be used to manufacture any of the components of the device 10. As used herein, the phrase additive manufacturing technique refers to any additive manufacturing technique or process that builds three-dimensional objects by adding successive layers of material on a material. The additive manufacturing technique may be performed by any suitable machine or combination of machines. The additive manufacturing technique may typically involve or use a computer, three-dimensional modeling software (e.g., Computer Aided Design, or CAD, software), machine equipment, and layering material. Once a CAD model is produced, the machine equipment may read in data from the CAD file and layer or add successive layers of liquid, powder, sheet material (for example) in a layer-upon-layer fashion to fabricate a three-dimensional object. The additive manufacturing technique may include any of several techniques or processes, such as, for example, a stereolithography ("SLA") process, a fused deposition modeling ("FDM") process, multi-jet modeling ("MJM") process, a selective laser sintering ("SLS") process, an electronic beam additive manufacturing process, and an arc welding additive manufacturing process. In some embodiments, the additive manufacturing process may include a directed energy laser deposition process. Such a directed energy laser deposition process may be performed by a multi-axis computer-numerically-controlled ("CNC") lathe with directed energy laser deposition capabilities.

The figures and description provided herein depict and describe preferred embodiments of handheld medical device for accessing a body cavity for purposes of illustration only. One skilled in the art will readily recognize from the foregoing discussion that alternative embodiments of the components illustrated herein may be employed without departing from the principles described herein. Thus, upon reading this disclosure, those of skill in the art will appreciate still additional alternative structural and functional designs for the handheld body cavity access device. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the methods and components disclosed herein without departing from the spirit and scope defined in the appended claims.

What is claimed:

1. A handheld body cavity access device, the device comprising:
   a handle including a distal end, a proximal end, and a longitudinal axis extending between the distal and proximal ends, the handle having a cavity aligned with the longitudinal axis;
   a trocar including a proximal end coupled to the handle;
   a dilator assembly at least partially disposed within the trocar and having a distal end and a dilator hub at least partially disposed in the cavity of the handle, the dilator hub including a tubular portion and a flange extending radially outward from the tubular portion;
   a blade assembly at least partially disposed within the dilator assembly;
   a spring disposed in the cavity of the handle and biased against the dilator hub;
   wherein the dilator assembly is movable between a retracted position, in which a distal end of the blade assembly extends from the distal end of the dilator assembly and the spring is in a compressed position, and an extended position, in which the distal end of the blade assembly is covered by the distal end of the dilator assembly and the spring is in an expanded position;
   wherein the spring engages a spring seat defined by an outer surface of the flange of the dilator hub,
   the device further comprising a needle assembly coupled to the handle by a lock so that when the needle assembly is in a locked position, the needle and handle are movable together, and when the needle assembly is in an unlocked position, the handle is movable axially relative to the needle.

2. The device of claim 1, wherein the dilator hub has a symmetrical cross-section about the longitudinal axis.

3. The device of claim 1, wherein the dilator assembly includes a shaft having a bore and a tapered portion at the distal end of the dilator assembly, wherein the dilator hub is at least partially disposed in the bore of the shaft at a proximal end of the shaft.

4. The device of claim 1, wherein the blade assembly includes a blade hub disposed in the cavity of the handle and having a body defining a bore aligned with the longitudinal axis and a tab extending away from the longitudinal axis of the handle.

5. The device of claim 4, wherein the spring engages the spring seat of the dilator hub and a spring seat defined by the body of the blade hub.

6. The device of claim 4, wherein the spring at least partially surrounds a portion of the blade hub.

\* \* \* \* \*